United States Patent [19]

Ruddock

[11] 4,311,689
[45] Jan. 19, 1982

[54] METHOD AND CONTAINER FOR PRODUCTION OF DIAGNOSTIC SCANNING

[75] Inventor: Clinton F. Ruddock, Amersham, England

[73] Assignee: The Radiochemical Centre Limited, England

[21] Appl. No.: 16,617

[22] Filed: Mar. 1, 1979

[30] Foreign Application Priority Data

Mar. 2, 1978 [GB] United Kingdom ............... 08370/78

[51] Int. Cl.³ .................... A61K 43/00; A61K 49/00; B65D 71/00

[52] U.S. Cl. .......................................... 424/1; 422/61; 424/9

[58] Field of Search ............... 424/1, 12, 9; 23/230 B; 422/61

[56] References Cited

U.S. PATENT DOCUMENTS

| | | | |
|---|---|---|---|
| 3,749,556 | 7/1973 | Barak et al. | 424/1 |
| 3,902,849 | 9/1975 | Barak et al. | 424/1 |

OTHER PUBLICATIONS

Ikeda et al., J. Nucl. Med., 17 (5), 1976, pp. 389–393.
Persson, Int. J. Appl. Rad. Isotopes, vol 28, 1977, pp. 97–104.
Persson, Nucl. Medizin, 13 (1975) pp. 389–399.

*Primary Examiner*—Benjamin R. Padgett
*Assistant Examiner*—Christine M. Nucker
*Attorney, Agent, or Firm*—Wenderoth, Lind & Ponack

[57] ABSTRACT

A closed container for producing, on introduction of a solution of technetium-99m as pertechnetate, technetium in a form suitable for diagnostic scanning, contains under sterile conditions tin or a tin-containing alloy as a reducing agent for the pertechnetate and a complexant for the reduced technetium, the contents of the container being present in a dry state. In the method, the pertechnetate solution, suitably the eluate in isotonic saline from a technetium-99m generator, is added to the container and the complex recovered therefrom.

9 Claims, No Drawings

METHOD AND CONTAINER FOR PRODUCTION OF DIAGNOSTIC SCANNING

This invention relates to a method and container for bringing technetium-99 m into a form suitable for diagnostic scanning. The technetium-99 m isotope is conveniently available in solution in the form of the chemically stable pertechnetate ion ($TcO_4^-$). Aqueous solutions of pertechnetate ion are eluted, frequently by a saline eluent, from generators containing the long-lived parent molybdenum-99. Pertechnetate itself has only limited applications in diagnostic scanning because it does not readily form complexes with materials which locate in specific parts of the body. It has therefore long been general practice to reduce technetium from the 7-valency in pertechnetate to the 3-, 4- or 5-valency in which it readily forms complexes with a wide variety of materials. Many reducing agents have been tried over the last twenty years for this purpose, but the current reducing agents of choice are stannous salts (e.g. chloride, fluoride or tartrate). Despite widespread commercial utilisation, stannous reducing agents suffer from a number of serious disadvantages:

(i) Stannous salts are unstable during production, storage and after labelling, both with respect to hydrolysis in solution and to oxidation. This leads to losses caused by oxidation and to labelled impurities as a result of hydrolysis.

(ii) Stringent precautions need to be taken by the manufacturer to minimise oxidation, including nitrogen purging of all solutions used in preparation and of vials sent out to customers.

(iii) To compensate for expected losses of stannous ions, manufacturers tend to use a very large stoichiometric excess. Tin is known to be toxic, so the use of a large excess is undesirable.

(iv) Without these precautions, the shelf life of vials containing stannous salts as reducing agents is generally poor, and even with them is occasionally less than is desired.

It is an object of this invention to avoid these problems by the use of a metallic reducing agent for the pertechnetate. It is known that certain metals are capable of reducing pertechnetate; or to put it another way, that pertechnetate, which has properties similar to permanganate, is capable of oxidising certain metals. U.S. Pat. No. 3,749,556 describes a process in which a generator eluate containing dissolved pertechnetate is passed down a column of particulate metal, e.g. iron or tin, where it is reduced and adheres to the metal. The technetium is then recovered by means of a further eluent having a pH less than 6 and containing a complexant for the technetium. The method of the U.S. Patent involves two reaction stages, a column of ion-exchange material in addition to the column of particulate metal, and an acidic eluent, and has, so far as we know, never been used commercially. Our experiments involving reduction of pertechnetate with metals indicate that, unless special precautions are taken, the reduced technetium adheres to the surface of the metal and cannot be satisfactorily recovered.

Ikeda et al, J. Nucl. Med., 1976, 17, No. 5, 389-93 describes the electrochemical reduction of pertechnetate in the presence of an aqueous solution of phytic acid, with formation of technetium phytate, using Pt-Sn or Sn-Sn electrodes made by attaching pieces of the metals to the end of magnetic stirring bars and coating them with polypropylene. The technique described involved mixing the pertechnetate and phytate aqueous solutions, adding the magnetic stirring bar and stirring. This was adequate as a laboratory technique, although it did not apparently work when EDTA was substituted for phytate, but is complex and otherwise unsuitable for commercial operation. The magnetic stirring bar of Ikeda is complex and has proved to be unnecessary. Furthermore, for commercial purposes, it is necessary that the phytate or other complexant and the tin or other metallic reductant should be provided under sterile conditions in a single container to which the user simply adds pertechnetate solution; and it is necessary that the contents of the container should be dry, as otherwise corrosion problems involving the metallic reductant inevitably arise and reduce the shelf life of of the container.

B. R. R. Persson, International Journal of Applied Radiation and Isotopes, 1977, Volume 28, pages 97-104 describes a process for labelling plasmin with technetium by reducing pertechnetate with stannous chloride in the presence of the plasmin. In a section on page 100 in which stannous chloride concentration was the variable investigated, he performed one experiment using tin metal in place of stannous chloride at a pH of 2. The result was rather poor and was assessed as equivalent to a stannous chloride concentration of 0.015 mM. Tin is quite readily soluble in aqueous media at pH 2. It appears that Persson was using tin metal for the in situ preparation of stannous chloride. By contrast, the present invention uses tin metal as a reducing agent under conditions in which it is not appreciably soluble in the liquid medium.

The present invention provides in one aspect a method of treating a solution of technetium-99 m as pertechnetate to bring the technetium into a form suitable for diagnostic scanning, which method comprises:

(a) providing a container containing under sterile conditions, tin or a tin-containing alloy as a reducing agent for the pertechnetate, and a complexant for the reduced technetium, the contents of the vessel being present in a dry state.

(b) aseptically introducing into the vessel the pertechnetate solution, thereby forming a liquid mixture having a predetermined pH in the range 3 to 12, (c) and recovering a complex of technetium with the complexant therefor.

The solution of pertechnetate is conveniently the sterile eluate from a technetium generator, e.g. an aqueous solution of pertechnetate normally in isotonic saline. The precise nature of the solution is not critical, and generally no pre-treatment of the solution is required.

When the mixture contains a complexant for technetium, the technetium, upon reduction from the 7+ valency to a lower valency state, becomes attached to the complexant. In general, the nature of the attachment is not precisely known, though it is believed that electron donation from the complexant (donor ligand) to the technetium (acceptor ion) is involved. In many cases there is chromatographic evidence for more than one Tc-complex species. The compounds which may be labelled with technetium-99 m in this way are herein called complexants. A large number of them suitable for use in this invention are available for diagnostic scanning of different parts of the body, as the following non-exhaustive list indicates:

1. Brain scanning—Diethylenetriamine penta acetate (DTPA), gluconate, glucoheptonate.
2. Kidney scanning—DTPA, gluconate, glucoheptonate, dimercaptosuccinate (DMSA), citrate.
3. Bone scanning—Methylenediphosphonate (MDP), pyrophosphate.
4. Myocardial infarct scanning—MDP, pyrophosphate.
5. Hepatobiliary scanning—N-2, 6-(dimethyl phenyl) carbamoylmethyliminodiacetic acid (HIDA), diethyl HIDA.
6. Deep vein thrombus detection (DVT)—Fibrinogen, streptokinase, urokinase.
7. Blood pool visualisation—human serum albumin.
8. Lung—macroaggregated albumin, albumin microspheres.
9. Liver—stabilised colloids, e.g. colloidal sulphur stabilised by gelatin, PVP, dextran.
10. Other—amino acids, thioglucose, thiomalate.

The requirements for the metallic reducing agent are that it should be capable of reducing pertechnetate at an acceptable rate, and that it should not itself be significantly soluble in, or significantly reactive with any other component of, the liquid mixture formed by addition of the pertechnetate solution. Tin reduces pertechnetate at a rapid rate and is satisfactorily inert to other components of the mixture. Alloys of tin may be used and may be advantageous.

Commercial or analytical grade tin may be used in the method with success, but 99.999% purity tin is less reliably reactive. Possibly the chemical reactions, which are believed to take place on the metal surface rather than in the liquid medium, are assisted by the presence of trace qualities of other metals or surface imperfections which form microscopic electrochemical cells. Alloys of tin with other metals are reliable and effective reducing agents. Since the amount of pertechnetate to be reduced is very small, the proportion of tin in the alloy determines to some extent the rate of reduction but is not otherwise critical and alloys containing as little as 5% tin are useful. Alloys of tin with gold, mercury, silver and lead, (e.g. solder) are suitable, and among these alloys of 0.5% to 10% by weight silver, balance tin, are particularly satisfactory and reliable. Alloys may have advantages over tin, other than improved reactivity and reliability, for example better mechanical strength, malleability and resistance to corrosion.

Since the amount of pertechnetate introduced into the mixture is very small, the amounts of complexant and metallic reducing agent present will necessarily be greatly in excess of the stoichiometric and are not critical. Amounts of from 1 mg. to 1 g. of complexant are likely to be satisfactory for handling the product of one elution, e.g. from 0.5 to 50 ml. and typically 1 to 15 ml., of a commercial technetium generator. The surface area of the metallic reducing agent present determines the rate of reduction of the pertechnetate; enough tin should be used to ensure reduction in a conveniently short time. From 0.1 to 10 cm$^2$ is generally sufficient; for example, we have found that a piece of analytical reagent grade granular tin (99.9%) weighing 100–200 mg., or a piece of analytical grade tin foil measuring 0.5 cm.×1 cm.×0.25 mm., is sufficient to effect complete reduction of 100 mCi of pertechnetate in 5–10 minutes in the presence of a suitable complexant.

The pH of the mixture formed should be in the range from 3–12, since outside this range tin is to some extent soluble in aqueous media. The pH of the mixture can be adjusted, e.g. by means of a solid buffer in the container or by the addition of acid or alkali to the pertechnetate solution, to a value which is optimum for the complexant being used. This is a very valuable feature of the invention, since there are many materials, e.g. proteins, which may form more stable complexes with technetium under alkaline conditions; these have hitherto not been utilized since the use of a stannous salt as a reducing agent requires acid or neutral conditions.

In another aspect, the invention provides a closed container for producing, on introduction of a solution of technetium-99 m as pertechnetate, technetium in a form suitable for diagnostic scanning, containing under sterile conditions tin or a tin-containing alloy as a reducing agent for the pertechnetate, and a complexant for the reduced technetium, the contents of the container being present in a dry state.

For the preparation of diagnostic scanning agents, reagent mixtures are frequently supplied in bottles each closed by a pierceable autoclavable closure and containing individual doses of reagents in a dry state intended to be activated by injection of the pertechnetate solution eluted from a generator. According to the present invention, the complexant for technetium may be metered into each individual bottle, either as a solution or dispersion followed by freeze drying, or by dry dispensing, e.g. as a powder or tablet. The metal may be present in a convenient form such as foil, granules, wire or shot, and may be loose in the vessel. The use of loose metal powder is not recommended because of the risk that the powder may be drawn up by the hypodermic syringe used to extract the diagnostic scanning solution from the vessel. Alternatively the metal may be provided as a coating, e.g. by coating, on the internal walls of the vessel or on an inert support; for example, inert plastics spheres, suitably 0.3 to 1.0 cm. diameter, may first be rendered electrically conducting, e.g. by vacuum evaporation of gold, and then electroplated with tin. Alternatively again, the metal may be carried by or associated with the pierceable autoclavable closure, in which case inversion of the vessel would be necessary to form the mixture and effect reduction of the pertechnetate.

Our preferred arrangement is to fix the tin or tin alloy to a piece of flexible chemically inert foil, e.g. of stainless steel or a plastics material such as cellulose acetate, and to position the foil in curved configuration round the inside wall of the bottle. For example a piece of tin foil may be stuck to the flexible foil with adhesive, or tin metal may be electroplated on to the foil if necessary via an intermediate metal. The foil itself should be sufficiently elastic to be held in curved configuration by friction round the wall of the bottle. Positioning the tin in the bottle in this way has advantages. First, it may be positioned near the bottom of the bottle so as to be immersed in the pertechnetate solution when the bottle is upright; or it may be positioned near the neck of the bottle so as to be immersed in the pertechnetate solution only while the bottle is tilted; this may be useful if it is desired to dispense the complexant as a liquid and lyophilise it in the bottle without permitting it to contact the tin, or if it is desired to contact the pertechnetate solution with the tin only for a limited period of time. Second, it is out of the way so there is no danger that a technician who uses a hypodermic syringe to withdraw liquid will stick the needle into metal or plastics material.

The tin or tin alloy should be degreased to render it wettable. It may also be activated by removal of the oxide layer, for example by immersing in concentrated hydrochloric acid followed by washing in ethanol. Good results can be achieved without activation however.

Providing the contents of the container in the solid state gives rise to an improvement in reliability and possibly also shelf life. Even if the complexant is in physical contact with the tin reducing agent, solid state chemical reactions and corrosion or oxidation of the metal are unlikely to take place to any significant extent.

Other materials may be included in the container. A buffer may be provided to control the pH of the liquid mixture formed by addition of the pertechnetate solution at a desired value in the range 3 to 12; suitable buffers are physiologically acceptable materials known in the art such as phosphate, TRIS-buffer, bicarbonate, acetate. Preservatives and antioxidants may be used. The closed container may contain nitrogen or some other inert gas in place of air. When the technetium complex is lipophilic, it may be useful to add a water-miscible organic solvent such as ethanol; however, this should be added together with, or just before, the pertechnetate solution.

It is an advantage of this invention that only a single piece of metal need be used; of course, more than one piece may be used, but no advantage in performance is gained, whether or not the pieces are maintained in electrical contact. It is preferred to use a fresh piece of metal for each reduction; if one piece of metal is used repeatedly surface deactivation may become a problem.

The present invention has the following advantages over the conventional reduction method using stannous salts:

(i) Problems of stannous salt instability during production, storage and after labelling are eliminated—reducing both losses by oxidation and labelled impurities due to hydrolysis.

(ii) Production procedures are simplified e.g. by the use of cut metal foil or coated vials and powder dispensed ingredients.

(iii) It is no longer necessary, though it may still be advantageous, to nitrogen purge vials before sterilisation.

(iv) It reduces toxicity, because the only tin solubilised is the minute amount oxidized in reducing the pertechnetate. Since it is not necessary to have a large excess of stannous salt present in the solution to compensate for losses, it is not necessary to provide additional amounts of complexant to complex the stannous salt, and it is therefore possible to use smaller quantities of all ingredients.

(v) The shelf life of diagnostic scanning kits may be dramatically improved.

(vi) The metal reducing agent may be subjected to sterilisation by $\gamma$-irradiation without deteriorating, unlike certain stannous salts.

(vii) The labelling technique can be performed over a wide pH range, and particularly in alkaline solution thus giving rise to the possibility of labelling new molecules.

(viii) The technique should be unaffected by technetium-99 in the technetium-99 m.

(ix) Virtually no stannous ion is present in vivo such as might interfere with a subsequent test.

While the invention is of value as a quick, reliable and simple route to all technetium complexes that are used for diagnostic scanning, it is of particular advantage in the following areas:

(a) Where the tin compound with the complexing agent is insoluble in water, for example aluminon. In such cases, stannous salts could not readily be used as reductants (b) Where an alkaline pH needs to be maintained in order to label the complexant, for example proteins.

(c) Where the reaction between the reduced technetium and the complexant is slow in comparison with the rate of hydrolysis and/or oxidation of an alternative stannous salt reducing agent, for example saccharic acid and sugars generally. In such cases, the use of stannous salts as reducing agents tends to result in the formation of a colloidal dispersion of unreactive technetium dioxide.

(d) Where the complexant ligand is weak and liable to hydrolyse in the absence of an excess of the complexant, e.g. gluconate.

The following Examples illustrate the invention. Except where indicated, the metallic reducing agent was a $5 \times 10$ mm. piece of tin foil 0.1 mm. thick of 99.5% purity manufactured by British Drug Houses, which was degreased and then activated before use by immersion for 1 minute in concentrated hydrochloric acid followed by washing in ethanol. These laboratory experiments were not performed under sterile conditions, and in some cases pH adjustment was effected immediately after addition of the pertechnetate solution. For commercial operation, however, the buffer would normally be predispensed in dry form along with the complexant and the metallic reducing agent. In all cases, the pertechnetate solution was 1 ml. of the isotonic saline eluate from a technetium-99 m generator. Measurement of the extent of complex formation was by thin layer chromatography on silica gel, by means of elution, first with methylethyl ketone and then with isotonic saline solution.

EXAMPLE 1

To a vessel containing a piece of tin foil, 1.3 mg. of citric acid and sodium bicarbonate buffer was added 1 ml. of pertechnetate solution. The pH was 6. The liquid mixture was left for 15 minutes. Labelling efficiency was 98%.

The complex was injected into rats which were sacrificed 2 hours post injection. Bio-distribution showed about 11% of activity retained in the kidneys and over 70% excreted in the urine with no significant concentration in any other organ.

This experiment was repeated at different pH values; first at the natural pH of the mixture without the sodium bicarbonate, which was about 3.0; second at a pH of 11 using sodium hydroxide for adjustment. In both cases, complexes were obtained at high labelling efficiencies.

EXAMPLE 2

To a vessel containing a piece of tin foil, 12 mg. of d-glucose and sodium acid sulphate buffer was added 1 ml. of pertechnetate solution. The liquid mixture had a pH of 4 and was left for 15 minutes. Labelling efficiency was 80%.

The complex was injected into rats which were sacrificed 2 hours post injection. Bio-distribution showed about 5% liver and 29% kidney retention, with the bulk of the injected activity being excreted in the urine.

EXAMPLE 3

To a vessel containing a piece of tin foil and 0.8 mg. of partly neutralised (with sodium hydroxide) diethylenetriamine penta-acidic acid was added 1 ml. of pertechnetate solution. The pH was 4.3. The liquid mixture was left for 15 minutes. Labelling efficiency was greater than 98%.

Bio-distribution in rats at 2 hours post injection indicated excretion in the urine of greater than 95% of the injected activity.

EXAMPLE 4

To a vessel containing a piece of tin foil, 5 mg. of methylenediphosphonic acid and sodium bicarbonate buffer was added 1 ml. of pertechnetate solution. The pH was 6.0. The liquid mixture was left for 15 minutes. Labelling efficiency was 98.5%.

Bio-distribution in rats at 2 hours post injection indicated about 37% bone uptake and most of the remainder excreted in the urine.

EXAMPLE 5

This Example shows the use of ethanol to enhance the solubility of a relatively water-insoluble complexant.

To a vessel containing a piece of tin foil, 0.2 mg. of 8-mercapto-quinoline hydrochloride and sodium bicarbonate buffer was added a mixture of 0.8 mls. of pertechnetate solution with 0.2 mls. of ethanol. The pH was 4. The liquid mixture was left for 15 minutes. Labelling efficiency was greater than 98%.

Bio-distribution in rats at 2-hours post injection indicated about 37% liver uptake, 20% small intestine uptake and 15% muscle uptake with a small amount of urinary excretion and blood labelling.

EXAMPLE 6

This Example shows the successful labelling by the method of this invention of a material which is difficult to label with technetium by other techniques.

To a vessel containing 2 mg. of aluminon and a piece of tin foil was added 1 ml. of pertechnetate solution and the pH adjusted to 5 with acid. The liquid mixture was allowed to stand for 15 minutes. Essentially all the pertechnetate was reduced to give a complex of technetium with the aluminon.

EXAMPLE 7

To a vessel containing 10 mg. of disodium ethylenediamine tetra-acetic acid and a piece of tin foil was added 1 ml. of pertechnetate solution. The unadjusted pH was 4.0. The liquid mixture was allowed to stand for 15 minutes. At that time, reduction of the pertechnetate was complete and all the technetium activity was present as a complex with EDTA.

This experiment was repeated twice, at pH values 3.0 and 5.0, with the same results.

EXAMPLE 8

It may not be convenient in commecial operation to activate the metal reducing agent immediately before use. This and the following Example show how a tin-silver alloy containing 3.5% silver, balance tin, can be used to achieve high labelling efficiencies even in difficult cases and without pre-treatment. A piece of tin foil was degreased and activated by immersion for 1 minute in concentrated hydrochloric acid followed by washing with ethanol, and was then added to a vessel containing 5 mg. of oxalic acid, followed by 1 ml. of pertechnetate solution. The liquid mixture was adjusted to pH 4.7 with base and allowed to stand for 15 minutes. Labelling efficiency was 89%.

In another experiment, the above procedure was followed, except that the piece of tin foil was merely degreased but was not activated in hydrochloric acid. Variable low yields around 40% of complex were obtained.

In a third experiment, a piece of 3.5% silver-tin alloy was degreased but not activated and then used under the above conditions. Labelling efficiency was 88%.

EXAMPLE 9

A piece of tin foil was degreased but not activated and was added to a vessel containing 2 mg. rhodizonic acid followed by 1 ml of pertechnetate solution. The liquid mixture was adjusted to pH 3.7 with acid and allowed to stand for 15 minutes. Labelling efficiency was 78%.

In another experiment under the same conditions, a piece of 3.5% silver-tin alloy was used in place of the tin foil. Labelling efficiency was 94%.

EXAMPLE 10

This Example shows the effect of using different kinds of tin metal.

1 drop of 0.5 molar sodium citrate was mixed with 1 ml. of pertechnetate solution and the pH adjusted to 6 with acid. A 6×6 mm. piece of the tin foil, or a piece of granulated tin judged to have about the same surface area was added. Preparations were sampled at 5 minute intervals for analysis, and the results are set out in Table 1 below.

TABLE 1

| | % Complex Formation | | | |
| --- | --- | --- | --- | --- |
| | Interval from start of Experiment | | | |
| Tin | 5 m. | 10 m. | 15 m. | 20 m. |
| 1 | 90% | 97% | | |
| 2 | 20% | 51% | 73% | 84% |
| 3 | 15% | 50% | 75% | 89% |
| 4 | 78% | 97% | 98% | |

Materials:
1. British Drug Houses 'Analar' granulated Sn - total foreign metals 0.04% max, degreased.
2. British Drug Houses Sn foil (0.1 mm.) - 99.5% purity, degreased.
3. Marz Sn foil (0.12 mm.) - 99.999% purity, degreased.
4. Marz Sn foil as 3. but activated for 1 minute in HCl, washed in ethanol and left for 24 hours.

In a further experiment to examine the effect of increasing the surface area of the tin, the same conditions were observed as for the above experiments, but a 24×6 mm. piece of Marz foil was used. Complete reduction was observed at 5 minutes.

EXAMPLE 11

To 0.1 ml. of 0.1 M. disodium EDTA was added 1 ml. of pertechnetate solution. The pH was 4.3 and was not adjusted. A 2 cm. length of 14 swg solder wire (70% Sn-Pb) was degreased in ethanol and then immersed in the liquid mixture which was left for 15 minutes. Labelling efficiency was 93%.

EXAMPLE 12

6.4 mg of sodium gluconate was dissolved in 1 ml. of pertechnetate solution. A 2 cm. length of 12 swg tinned copper wire with cut ends was degreased and then immersed in the liquid mixture which was left for 15 minutes. The labelling efficiency was 96%.

EXAMPLE 13

By the general technique of Examples 1 to 5 we have prepared technetium complexes of a total of 91 different complexants. The following list gives representative examples. In each case the pH used and the labelling efficiency achieved are indicated.

|   | Class and Compound | pH | Labelling Efficiency % |
|---|---|---|---|
| A | Aliphatic carboxylic acids | | |
|   | citric acid | 3–11 | 98 |
| B | Sugars and sugar derivatives | | |
|   | d-glucose | 4 | 80 |
| C | Amino acids and proteins | | |
|   | human serum albumin | 7 | 90 |
| D | Iminodiacetic acid derivatives | | |
|   | ethylenediamine tetra-acetic acid | 3–5 | 98 |
|   | diethylene triamine penta-acetic acid | 4 | 98 |
|   | N-2,6-(diethylphenyl)carbamoylmethyl iminodiacetic acid (E-HIDA) | 5 | 98 |
| E | Phosphorus compounds | | |
|   | methylene diphosphonic acid | 4 | 90 |
| F | Dyestuffs and indicators | | |
|   | aluminon | 6 | 80 |
| G | Sulphur compounds | | |
|   | glutathione | 6 | 80 |
| H | Hydroxamic acids | | |
|   | rhodotorulic acid | 4 | 91 |
| I | Catechol derivatives | | |
|   | 2,3-dihydroxybenzoic acid | 4 | 96 |
| J | Amines | | |
|   | cyclam | 11.5 | 80 |
| K | Miscellaneous | | |
|   | sodium fluoride | 6 | 75 |

I claim:

1. A method of treating a solution of technetium-99 m as pertechnetate to bring the technetium into a form suitable for diagnostic scanning, which method consists essentially of:
    (a) providing a vessel containing under sterile conditions tin or a tin-containing alloy as a reducing agent for the pertechnetate, and a complexant for the reduced technetium, the contents of the vessel being present in a dry state,
    (b) aseptically introducing into the vessel an aliquot of a solution containing pertechnetate ions, thereby forming a liquid mixture having a predetermined pH in the range 3 to 12 and containing a complex of technetium with a complexant therefor,
    (c) and aseptically withdrawing from the vessel at least part of said aliquot comprising a complex of technetium with the complexant therefor.

2. A method as claimed in claim 1, wherein the pertechnetate solution is an aqueous saline solution of pertechnetate obtained by elution of a technetium-99 m generator.

3. A method as claimed in claim 1, wherein there is used a tin alloy containing 0.5% to 10% by weight silver, balance tin.

4. A method as claimed in claim 1, wherein there is provided in the vessel from 1 mg. to 1 g. of the complexant and metal having a surface area of from 0.1 to 10 $cm^2$, and there is introduced into the vessel from 0.5 to 50 ml. of pertechnetate solution.

5. A method as claimed in claim 1, wherein there is also present in the container a buffer to keep the pH of the liquid mixture formed by introduction of the pertechnetate solution in the range 3 to 12.

6. A method as claimed in claim 1, wherein the tin or tin alloy is fixed to a piece of flexible chemically inert foil, which flexible foil is positioned in curved configuration round the inside wall of the container.

7. A closed container for producing, on introduction of a solution of technetium-99 m as pertechnetate, technetium in a form suitable for diagnostic scanning, containing under sterile conditions tin or a tin-containing alloy as a reducing agent for the pertechnetate, a complexant for the reduced technetium, and a buffer to keep the pH of the liquid mixture formed by introduction of the pertechnetate solution in the range of 3 to 12, the contents of the container being present in a dry state.

8. A container as claimed in claim 7, wherein the tin-containing alloy contains 0.5% to 10% by weight silver, balance tin.

9. A container as claimed in claim 7, wherein the tin or tin alloy is fixed to a piece of flexible chemically inert foil, which flexible foil is positioned in curved configuration round the inside wall of the container.

* * * * *